United States Patent [19]

Moret et al.

[11] Patent Number: 4,495,658

[45] Date of Patent: Jan. 29, 1985

[54] BIB HAVING A DUPLEX REFASTENABLE TAPE-TAB FASTENER

[75] Inventors: David M. Moret; Nicholas A. Ahr, both of Cincinnati, Ohio

[73] Assignee: The Procter and Gamble Company, Cincinnati, Ohio

[21] Appl. No.: 465,237

[22] Filed: Feb. 10, 1983

[51] Int. Cl.$^3$ .............................................. A41B 13/10
[52] U.S. Cl. ..................................... 2/49 R; 428/343
[58] Field of Search ....................... 2/49 R, 48, 243 B; 428/343

[56] References Cited

U.S. PATENT DOCUMENTS

| Re. 24,043 | 7/1955 | Barager | 2/49 |
|---|---|---|---|
| 2,782,420 | 2/1957 | Barager | 2/49 |
| 3,416,157 | 12/1968 | Marder et al. | 2/49 |
| 3,540,060 | 11/1970 | Brown | 2/49 |
| 4,186,744 | 2/1980 | Ness | 128/287 |

*Primary Examiner*—Doris L. Troutman
*Attorney, Agent, or Firm*—Thomas J. Slone; Fredrick H. Braun; Richard C. Witte

[57] ABSTRACT

A bib having a body member which obviates refastenable application of a tape-tab fastener directly to the front surface of the body member. The bib is provided with a duplex refastenable tape-tab fastener open by non-releasably securing a separability member on each side of a cut which extends from a neck-accommodating aperture in the body member to an adjacent outer edge of the bib; and by bridging the cut with an adhesive-faced tape-tab fastener by securing each of its oppositely disposed end portions to a separability member. The tape-tab fastener is said to be duplex by virtue of the construction enabling either end of the tape-tab to be peeled from its respective separability member: that is, both ends of the tape-tab fastener are refastenable. In a preferred disposable embodiment wherein the sheet material of the body member is a laminate comprising a topsheet lamina of relatively low tensile strength paper, the separability members are configured to have substantially greater areas than the ends of the tape-tab fastener in order to provide stress distribution between the tape-tab ends and the paper topsheet lamina; and to enable the bib to be fitted to a range of neck sizes. This construction also substantially obviates potential delamination of the topsheet lamina from the backsheet lamina due to imposing high stresses on the tape-tab fastener.

10 Claims, 6 Drawing Figures

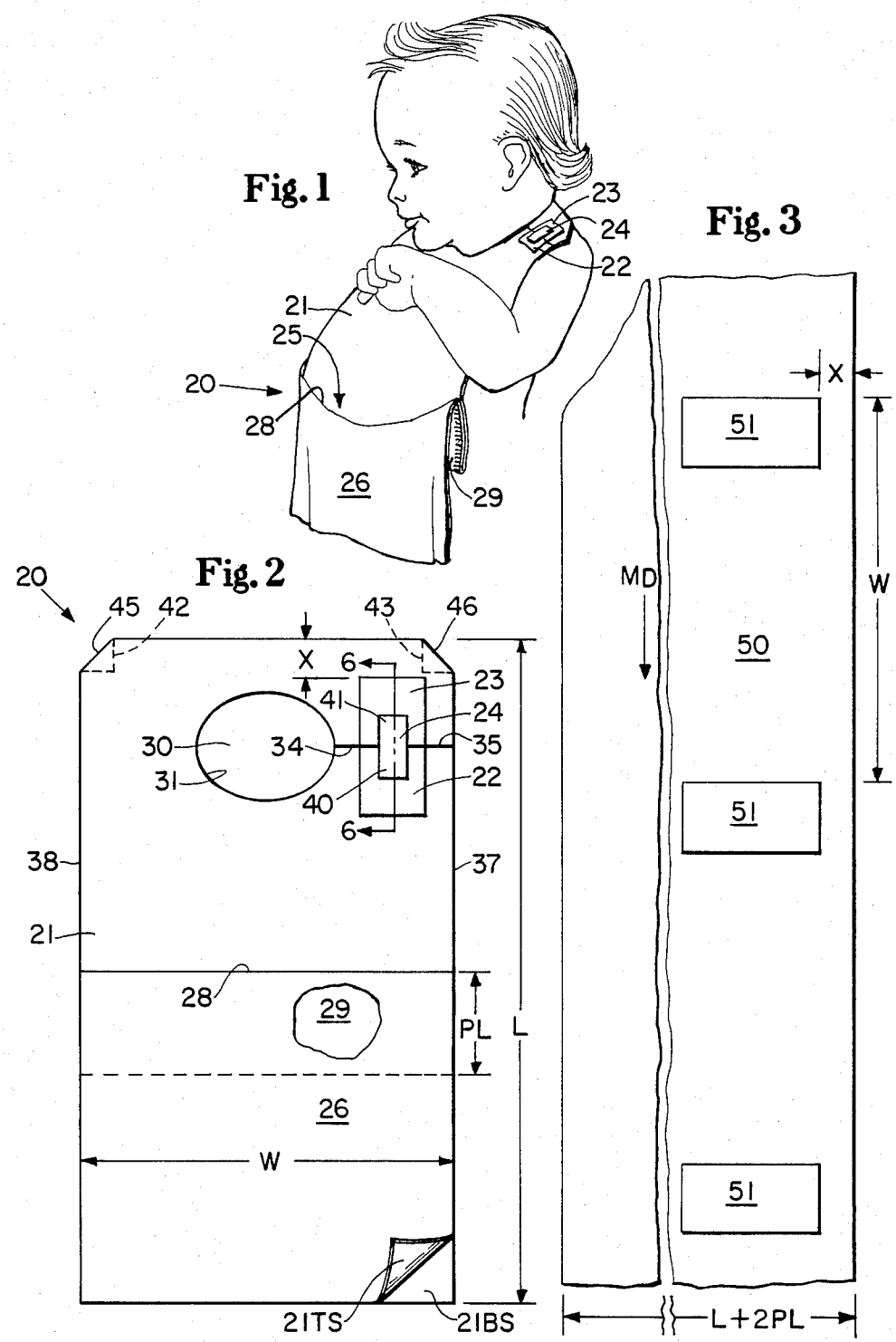

BIB HAVING A DUPLEX REFASTENABLE TAPE-TAB FASTENER

DESCRIPTION

1. Technical Field

This invention pertains to bibs--preferably disposable--for use on, for example, babies being fed. More particularly, it pertains to such bibs having refastenable tape-tab type fasteners which preferably are duplex in nature: that is, which can be opened or refastened by manipulating either of its oppositely disposed ends.

2. Background Art

U.S. Pat. No. 3,540,060 which issued Nov. 17, 1970 to G. W. Brown discloses a bib construction having refastenable, gripper-type fasteners. Additionally, bibs having refastenable tie-type fasteners are well known.

U.S. Pat. No. 3,416,157 which issued Dec. 17, 1968 to H. L. Marder et al discloses a disposable bib construction comprising a tape-tab fastener, as well as bib constructions which comprise double-faced pressure sensitive materials.

U.S. Pat. No. 4,186,744 which issued Feb. 5, 1980 to Irving S. Ness discloses a disposable diaper construction which comprises a Separability Member To Allow Disposable Diaper Openings And Re-Fastenings. Initially the separability member is adhesively secured to the mother's bond end of a tape-tab diaper fastener. Upon initial fastening, the separability member is adhered to the mother's bond region of the diaper; and, to open the fastener, its distal end is peeled from the separability member leaving the separability member secured to the motherr's bond region of the diaper.

U.S. Pat. 2,782,420 which issued Feb. 26, 1957 to E. D. Barager, and U.S. Pat. No. Re. 24,043 which issued July 26, 1955 to E. D. Barager disclose disposable bib constructions having neck-accommodating apertures and cuts which extend from the edges of their neck-accommodating apertures to adjacent outer edges of the bibs. These bibs further comprise closure means for bridging those cuts to secure the bibs on wearers thereof.

While the foregoing patents disclose bib constructions which have solved some of the felt needs for such products, they have not solved, in the manner of or degree of the present invention, the problems associated with providing bibs having refastenable fasteners: particularly with respect to providing laminated bib constructions having duplex tape-tab fasteners.

DISCLOSURE OF THE INVENTION

In accordance with one aspect of the invention, a bib is provided which comprises a duplex refastenable tape-tab fastener, either end of which may be peeled from an associated separability member which is non-releasably secured to the body member of the bib. Such separability members are disposed on opposite sides of a cut which extends from the edge of a neck-accommodating aperture to an adjacent outer edge of the bib body member, and are required in such bibs wherein the top surface of the bib body member is not sufficiently releasably compatible with the tape-tab fastener to provide refastenability. Additionally, the separability members may be substantially larger than adhesive faced ends of the tape-tab fastener to provide stress distribution from the tape-tab ends to the regions of the bib body member which underly the separability members.

BRIEF DESCRIPTIONS OF THE DRAWINGS

While the specification concludes with claims which particularly point out and distinctly claim the subject matter regarded as forming the present invention, it is believed the invention will be better understood from the following description taken in conjunction with the accompanying drawings in which:

FIG. 1 is an in-use perspective view of a disposable bib which is an exemplary embodiment of the present invention.

FIG. 2 is a plan view of the bib shown in FIG. 1, and wherein a bottom corner of the top lamina of its laminated body member is partially peeled back, and wherein a fragmentary portion of the apron panel has been torn away to reveal the front wall of the pocket of the bib.

FIG. 3 is a fragmentary plan view of a continuous web of laminated body member forming material after it has had unitary pieces of separability member material non-releasably secured to its front surface at bib-width-spaced intervals in the machine direction of a converter.

DETAILED DESCRIPTION OF THE INVENTION

Figure 4:
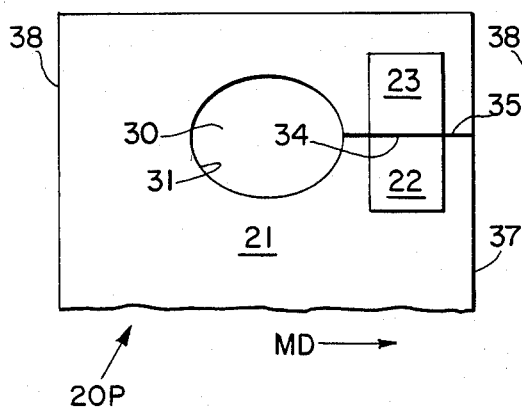
FIGS. 4 and 5 are fragmentary plan views of progressively more partially completed bibs as compared to the converting state shown in FIG. 3.

An exemplary bib which is a disposable embodiment of the present invention is designed 20 in FIG. 1. Bib 20 comprises body member 21, separability members 22 and 23, and a tape-tab fastener 24. As also shown in FIG. 1, bib 20 has a full-width pocket 25; and a portion of the body member 21 which is designated apron panel 26 pendulously depends from the upper edge 28 of the portion of the body member which forms the front wall 29 of pocket 25.

Referring now to FIG. 2 which is a plan view of bib 20, FIG. 1, the body member 21 has: a neck-accommodating aperture designated 30 which is defined by edge 31; transverse edges 34 and 35 formed by making a transverse cut intermediate edge 31 of aperture 30 and an adjacent portion of the outer edge 37 of bib 20. As shown in FIG. 2, portions of edges 34 and 35 are covered by tape-tab fastener 24, and the end portions 40 and 41 of tape-tab fastener 24 which are disposed on opposite sides of the transverse cut are secured to separability members 22 and 23, respectively. Alternatively, end portion 40 and 41 are referred to as tape-tabs because each is fastened to a different portion of the bib structure. Also, as shown, tape-tabs 40 and 41 are disposed in end-to-end relation.

Briefly, bib 20 is applied to a wearer by the user peeling either end of the tape-tab fastener 24 from its respective separability member so that the left shoulder portion of the bib can be separated sufficiently to fit the neck-accommodating aperture about the wearer's neck; and the tape-tab end is then refastened to the separability member from which it was peeled. By virtue of being able to unfasten and refasten both ends of the tape-tab fastener, the bib can easily be manipulated by both right-handed and left-handed persons in addition, of course, to the ambidextrous.

Referring again to FIG. 2, it also shows the top corners of body member 21 to have been folded under after which they were secured in the positions indicated by the dotted lines 42 and 43. Alternatively, the top corners could have been left square, or rounded, or simply cut off by diagonal cuts along the diagonal edges 45 and 46. As also shown in FIG. 2, a portion of the apron panel 26 has been torn away to show a portion of the front wall 29 of the pocket of the bib; and the laminated construction of body member 21 is indicated by a portion of the topsheet lamina 21TS being peeled back to reveal a portion of the backsheet lamina 21BS. The length and width of bib 20 are designated L and W, respectively, and the depth of the pocket of the bib is designated PL (i.e., pocket length).

Referring now to FIG. 3, an early stage in the converting of a web 50 of indeterminate length of body member forming sheet material is shown with its machine direction indicated by the arrow having MD adjacent thereto, and with pads 51 of separability member forming sheet material secured to the front surface of sheet material 50 at intervals having MD lengths of W, and spaced a distance X from the edge of the web. Thus, a web 50 having a width of L+2 PL is being forwarded so that discrete bib forming portions thereof are oriented with their width dimensions W oriented in the MD of the converter. While this orientation is desirable to effect a reduced line speed for a given number of bibs per minute as compared to having the bib length oriented in the MD, it is not intended to thereby limit the invention.

FIG. 4 is a fragmentary plan view of a partially converted bib designated 20P disposed downstream from the position in the converting apparatus where FIG. 3 was taken. As seen in this view, transverse cuts have been made across the entire web 50, FIG. 3, to sever a discrete body member 21 from the web. The newly formed edges of the body member 21 are designated 37 and 38. Also, the neck-accommodating aperture 30 having edge 31 has been cut, and a cut has been made through the body member 21 which cut extends from edge 31 to edge 37. The latter cut also subdivides the separability pad 51, FIG. 3, into separability members 22 and 23, and the edges formed in the body member 21 by the latter cut are designated 34 and 35. This latter cut enables a bib having a nominally sized neck-accommodating aperture 30 to fit a range of neck sizes, and to be fitted about a wearer's neck without having to be slipped down over the wearer's head.

Figure 5:
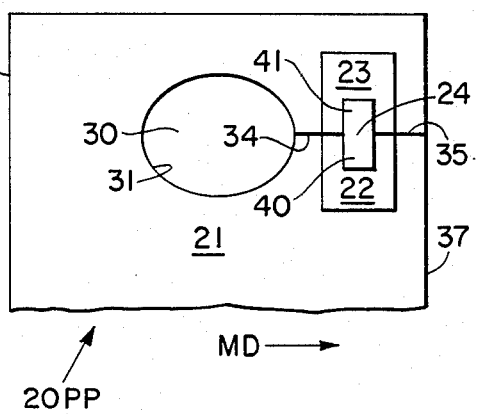

FIG. 5 is a fragmentary plan view showing a partially completed bib designated 20PP at a position in the converter downstream from the station in which the view of FIG. 4 was taken. In this view, a tape-tab fastener 24 having an adhesive coated face has been applied with its end portions 40 and 41 secured to the separability members 22 and 23, respectively. Thus, the tape-tab fastener 24 bridges the cut which severed the separability pad 51, and bridges between the separability members 22 and 23. The adhesive on the face of tape-tab fastener 24 is such that, with respect to the substrate of the fastener and the top surfaces of the separability members, each end of the fastener is releasably refastenable to its respective separability member, and so that the adhesive remains coated on the fastener when an end of the fastener is peeled from its separability member.

Figure 6:
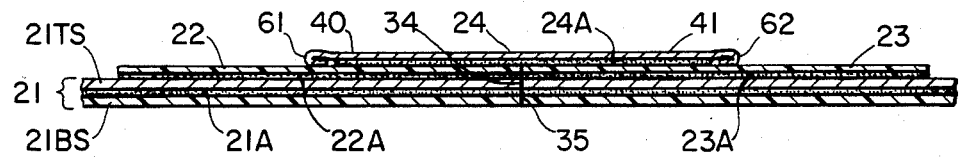
FIG. 6 is an enlarged scale fragmentary sectional view taken along line 6—6 of FIG. 2.

FIG. 6, taken along line 6—6 of FIG. 2, is a fragmentary sectional view wherein the thicknesses of the laminae 21TS and 21BS of the body member 21, the separability members 22 and 23, and the tape-tab fastener 24 are exaggerated as well as the intervening layers of adhesive: i.e., adhesive 21A intermediate lamina 21TS and lamina 21BS; adhesive 22A intermediate lamina 21TS and the separability members 22 and 23; and adhesive 24A intermediate the separability members 22 and 23 and the overlying ends 40 and 41 of the tape-tab fastener 24. As also shown in FIG. 6, both ends of tape-tab fastener 24 are turned under and secured to the fastener substrate to obviate their being adhesively secured to the separability members by adhesive 24A. Thus, both distal ends of the fastener 24 are formed into grasping portions 61 and 62 which are not secured to the underlying separability members in order to obviate the need for finger-nail initiation of peeling the tape-tab fastener open. However, it is not intended to thereby limit the present invention to including such unsecured grasping portions, or to this particular embodiment of grasping portions.

EXEMPLARY EMBODIMENT

An exemplary embodiment of bib 20, FIGS. 1 and 2, was made from a laminate comprising a one mil (about 0.0254 mm thick) polyethylene film (i.e., lamina 21BS), and a high-bulk paper lamina having a basis weight of about twenty-six pounds per three-thousand square feet (about 42.4 grams per square meter) and having a nominal caliper of about twenty-six mils (about 0.66 mm.). The laminae were adhesively secured together by National Starch Co. adhesive number NS 34-2857 which was applied with a rotogravure type applicator. The separability members were made from two mil Mylar (registered trademark of DuPont Co.), a polyester film having a good release surface with respect to the adhesive on the tape-tab-fastener stock. The tape-tab fastener was made from an adhesive coated substrate which was procured from Armak Company, Chicago, Ill., and designated by Armak as Adhesive Tape Type DT-1.

The exemplary bib has L, PL, W and X dimensions of about nineteen inches (about 48 cm), about three inches (about 7.6 cm), about eleven inches (about 28 cm), and about one inch (about 2.54 cm), respectively; the neck-accommodating aperture is oval-shape having a major diameter of about four inches (about 10 cm) and a minor diameter of about two-and-one-half inches (about 6.4 cm); the separability members were derived from pads 50, FIG. 3, having dimensions of about two inches (about 5 cm) by about four inches (about 10 cm) so that each separability member is about two inches (about 5 cm) by about two inches (about 5 cm). The tape-tab fastener of the exemplary bib has an adhesive coated length of about two inches (about 5 cm) and a width of about three-quarters of an inch (about 1.9 cm). Thus, the area of each separability member is about 5.3 times the adhesive coated area of its respective tape-tab end portion. This area ratio provides substantial stress distribution (i.e., reduction) from the relatively small tape-tab ends to the relatively low tensile strength paper topsheet lamina, in addition to enabling refastenability due to the release property of the separability members with respect to the tape-tabe ends. While this area ratio is 5.3 in the described exemplary bib, a ratio of two or greater is preferred; a ratio in the range of from about two to about six is more preferred; and a ratio of from about three to about five is most preferred. Also, by virtue of both the separability members having greater lengths, widths and areas relative to the tape-tab end portions, the bib can be applied to have a snug fit about a substantial range of neck sizes.

METHOD OF MAKING BIB 20

A method of making bib 20, FIGS. 1 and 2, is illustrated in part by the sequence of FIGS. 3 through 5. This includes applying non-releasable pads of separability member forming sheet material to an endless web of bib body member forming material at spaced intervals having a machine direction dimension equal to the width of a finished bib; cutting discrete body forming members from the web by machine-direction spaced transverse cuts, cutting a neck-accommodating aperture in said web adjacent each pad of separability material; cutting the web material along a line which extends from the edge of the neck-accommodating aperture to an adjacent outer edge of each discrete body member and so that the cut subdivides the pad of separability material into two discrete separability members; and applying a tape-tab fastener so that it spans the cut and bridges between the discrete separability members formed thereby. This enumeration of method steps is not intended to imply that the steps must be performed in the order stated. Indeed, it is presently contemplated that the preferred method will entail making the cuts to sever the discrete body forming members from the endless web after the other enumerated steps in order to maintain better control during the application and cutting of the separability pads, and the application of the tape-tab fasteners.

In addition to the above described features of an exemplary embodiment of the present invention and the method of making it, preferred embodiments of such bibs include full-width pockets (i.e., pockets which extend substantially the full width of the bibs); and apron panels which pendulously depend from the top edges of the front walls of the pockets. Such pendulously depending apron panels tend to cause such pockets to be self opening albeit bendable, form sustaining members may be incorporated in the bibs to enable manually shaping the pockets as desired.

While particular embodiments of the present invention have been illustrated and described, it would be obvious to those skilled in the art that various other changes and modifications can be made without departing from the spirit and scope of the invention. It is intended to cover in the appended claims all such changes and modifications that are within the scope of this invention.

What is claimed is:

1. A bib having a duplex refastenable tape-tab fastener having a non-adhesive grasping portion on each end thereof, and having one surface coated with an adhesive intermediate said grasping portions to provide two adhesive faced end tabs disposed in end-to-end relation, said bib further comprising means for refastenably securing said end tabs to spaced portions of said bib to secure said bib about the neck of a wearer, and for enabling either said end tab to be unfastened to remove said bib from the wearer.

2. A bib comprising a body member of sheet material having a front surface and a back surface, two separability members of sheet material each having a front face and a back face, and an adhesive-faced tape-tab fastener, said body member being comprised of material which obviates refastenable application of said tape-tab fastener directly to the front surface of said body member, said body member having a neck-accommodating aperture disposed adjacent the top end thereof and having a cut extending from the edge defining said aperture to an adjacent outer edge of said body member, said separability members comprising material which enables oppositely disposed end portions of said tape-tab fastener to be refastenably adhered to said from faces, said separability members being non-releasably secured to said front surface of said body member and so disposed that they are on opposite sides of said cut and adjacent thereto, said tape-tab fastener having one surface coated with an adhesive which enables refastenable adhesion to said front faces of said separability members, and said tape-tab fastener being configured and disposed to bridge across said cut and to bridge between said separability members when said end portions of said tape-tab fastener are adhesively secured to said front faces thereof.

3. The bib of claim 2 wherein said body member comprises a laminated sheet comprising a topsheet lamina of high bulk paper, a backsheet lamina, and means securing said laminae together, said separability members being sized and configured to substantially obviate tearing said topsheet lamina or delaminating said laminae upon unfastening either tape-tab end from its respective separability member.

4. The bib of claim 3 wherein each said separability member has an area of about two times or more than the adhesive coated area of its respective tape-tab end.

5. The bib of claim 3 wherein each said separability member has an area from about two to about six times the adhesive coated area of its respectie tape-tab end.

6. The bib of claim 3 wherein each said separability member has an area from about three to about five times the adhesive coated area of its respective tape-tab end.

7. The bib of claim 2 wherein said tape-tab fastener comprises non-adhesive grasping portions at both ends.

8. A method of making a bib having a duplex tape-tab fastener and which bib comprises a body member of sheet material having a surface property which obviates refastenable application of said tape-tab fastener directly to the front surface of said body member, said method comprising the steps of:
    non-releasably applying a pad of separability material to said body member adjacent an outer edge of said body member, said separability member having a top face which renders said tape-tab fastener refastenable thereto;
    cutting a neck-accommodating aperture in said body member adjacent one end thereof and adjacent said pad;
    cutting said body member and said pad along a line which extends from the edge of said neck-accommodating aperture to said outer edge so that said pad is subdivided into two discrete separability members and so that said body member can be manipulated to fit said neck-accommodating aperture about the neck of a wearer; and applying said tape-tab fastener so that it bridges between said separability members.

9. The method of claim 8 further comprising the steps of forwarding an endles web of body member forming material along a predetermined path, and cutting said web with spaced transverse cuts to subdivide it into discrete said body members.

10. The method of claim 9 wherein said transverse cuts are executed after said separability pads having been applied and subdivided into discrete separability members, and after said tape-tab fasteners have been applied.

* * * * *